US00PP33918P2

(12) United States Plant Patent
Koot

(10) Patent No.: US PP33,918 P2
(45) Date of Patent: Feb. 1, 2022

(54) ***ACER* PLANT NAMED 'SONKOOT6'**

(50) Latin Name: *Acer palmatum*
Varietal Denomination: SONKOOT6

(71) Applicant: Johannes Adrianus Maria Koot, Kaatsheuvel (NL)

(72) Inventor: Johannes Adrianus Maria Koot, Kaatsheuvel (NL)

(73) Assignee: BOTANIC EXPERIENCE B.V., Kaatsheuvel (NL)

( * ) Notice: Subject to any disclaimer, the term of this patent is extended or adjusted under 35 U.S.C. 154(b) by 0 days.

(21) Appl. No.: 17/351,171

(22) Filed: Jun. 17, 2021

(51) Int. Cl.
*A01H 5/00* (2018.01)

(52) U.S. Cl.
USPC ..... Plt./224

(58) Field of Classification Search
USPC ..... Plt./224
See application file for complete search history.

*Primary Examiner* — Annette H Para
(74) *Attorney, Agent, or Firm* — Penny J. Aguirre

(57) ABSTRACT

A new cultivar of *Acer palmatum* tree named 'SONKOOT6' that is characterized by its weeping plant habit, its young leaves that are purple-brown in color, its mature leaves that are dark green in color , and its foliage that is wine red in color in the fall.

2 Drawing Sheets

Botanical classification: *Acer palmatum.*
Variety denomination: 'SONKOOT6'.

CROSS REFERENCE TO A RELATED APPLICATION

This application is related to a European plant breeders' rights application filed on Dec. 7, 2018, application No. 2018/3259. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Acer palmatum* and will be referred to hereafter by its cultivar name, 'SONKOOT6'. 'SONKOOT6' is a deciduous tree grown for use as a landscape plant.

The new cultivar of *Acer* arose from a breeding program conducted by the Inventor in Kaatsheuvel, The Netherlands with the goal of developing an *Acer* cultivar with red leaves and a weeping plant habit. The new cultivar arose from a cross made in spring of 2012 between *Acer palmatum* 'Ryusen' (not patented) as the female parent and an unknown unnamed plant of *Acer palmatum* from the Inventor's breeding program as the male parent. The Inventor selected 'SONKOOT6' as a single unique plant amongst the seedlings that resulted from the above cross in spring of 2016.

Asexual propagation of the new cultivar was first accomplished by grafting onto *Acer palmatum* rootstock by the Inventor in Kaatsheuvel, The Netherlands in summer of 2016. Asexual propagation by grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'SONKOOT6' as a new and unique cultivar of *Acer.*

1. 'SONKOOT6' exhibits a weeping plant habit.
2. 'SONKOOT6' exhibits young leaves that are purple-brown in color.
3. 'SONKOOT6' exhibits mature leaves that are dark green in color.
4. 'SONKOOT6' exhibits foliage that is wine red in color in the fall.

The female parent plant of 'SONKOOT6' differs in having spring foliage that is green in color, summer foliage that is lighter green in color, and leaves that are slightly smaller in size. The male parent plant of 'SONKOOT6' differs in having a broadly spreading, upright plant shape and summer foliage that is red-purple in color. 'SONKOOT6' can be compared to the *Acer* cultivars 'Matsuyoi' (not patented) and 'Garnet' (not patented). 'Matsuyoi' is similar to 'SONKOOT6' in having a weeping plant habit. 'Matsuyoi' differs from 'SONKOOT6' in having spring foliage that is green in color, summer foliage that is bright green in color, and fall foliage that is orange in color. 'Garnet' is similar to 'SONKOOT6' in having a weeping plant habit and spring foliage that is purple-brown in color. 'Garnet' differs from 'SONKOOT6' in having a broad, mushroom-shaped plant habit, summer foliage that is purple-brown in color, and fall foliage that is bright orange-red in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying color photographs illustrate the overall appearance and distinct characteristics of the new cultivar as grown in Kaatsheuvel, The Netherlands.

Figure 1:
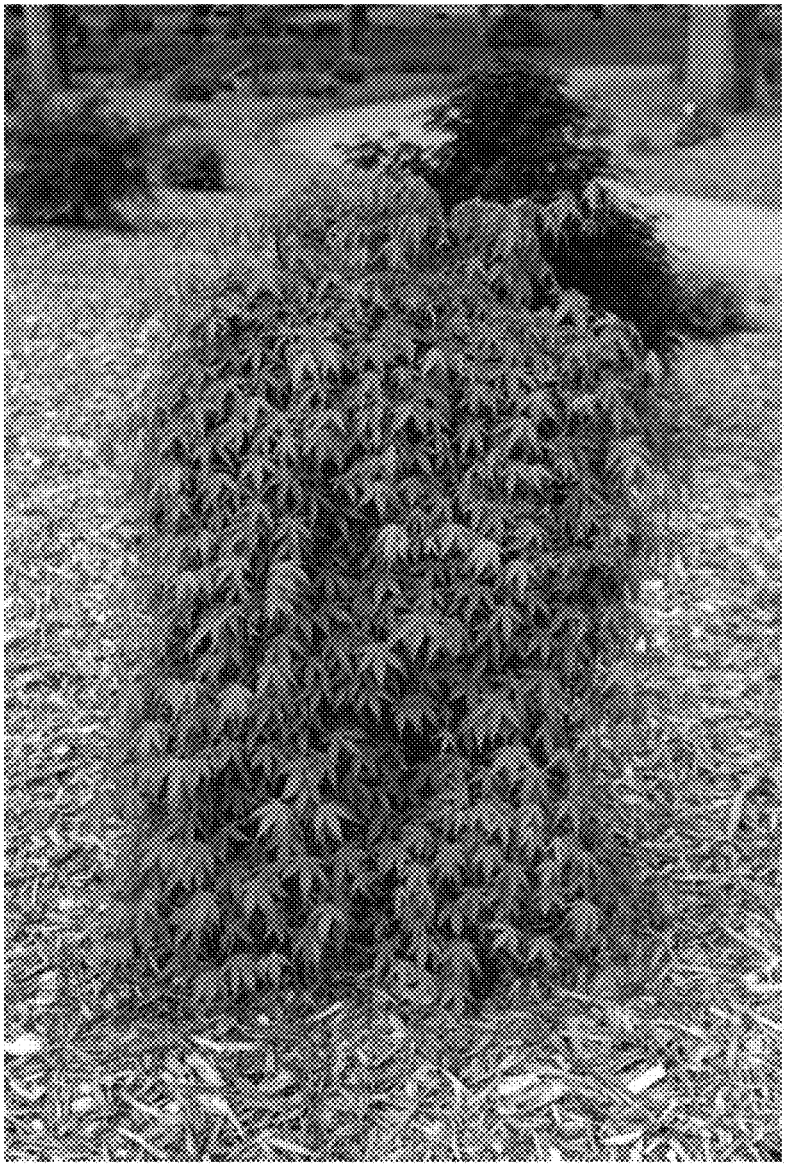
FIG. 1 provides an overall view of the foliage and plant habit of 'SONKOOT6' as a tree 5-years-in-age as grown outdoors.
Figure 2:
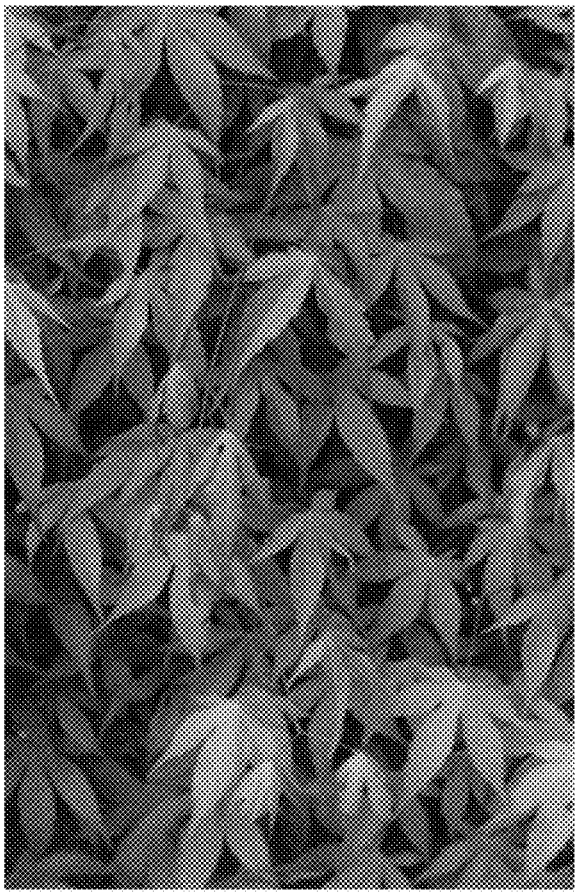

The photograph in FIG. 2 provides a close-up view of the young foliage of 'SONKOOT6' as a tree 5-years-in-age as grown outdoors.

Figure 3:
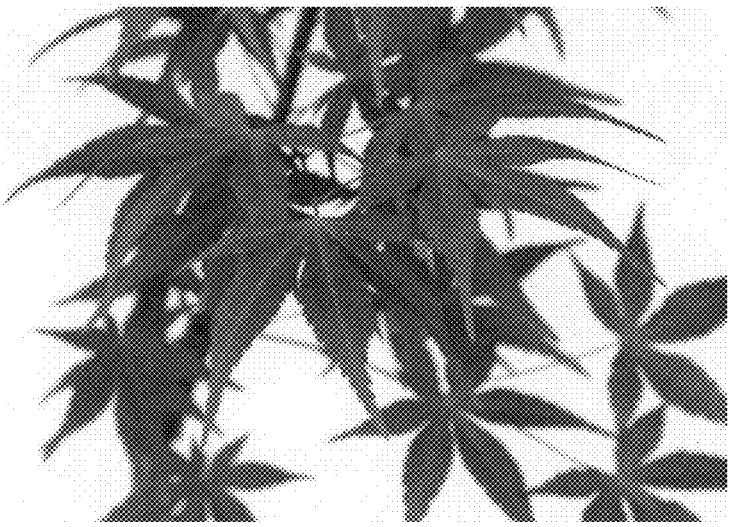

The photograph in FIG. 3 provides a close-up view of the mature leaves of 'SONKOOT6' as a tree 13-months-in-age as grown in a conventional greenhouse.

The colors in the photographs may differ slightly from the color values cited in the detailed botanical description, which accurately describe the colors of the new *Acer*.

DETAILED BOTANICAL DESCRIPTION

The following is a detailed description of 12-month-old trees of the new cultivar as grown in a greenhouse in 21-cm containers in Kaatsheuvel, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Deciduous shrub.

*Plant habit*.—Broadly weeping.

*Height and spread*.—Grafted onto standard 100 cm in height; an average of 130 cm in height and 100 cm in width.

*Cold hardiness*.—At least to U.S.D.A. Zone 6.

*Diseases and pests*.—No susceptibility or resistance to diseases or pest has been observed.

*Root description*.—Fibrous, freely branched.

*Propagation*.—Grafting.

*Root development*.—An average of 6 weeks needed for graft to connect to rootstock, 15 months to produce a young grafted plant.

*Growth rate*.—Moderately vigorous.

Branch description:

*Stem shape*.—Round.

*Stem size*.—An average of 25.3 cm in length, 2.5 mm in diameter.

*Stem surface*.—Slightly glossy.

*Stem color*.—Young; 184B, lower side 181B, mature; 176A, lower side a blend of 152D and 199B, internodes 152D and 199B, older stems; N199A.

*Stem strength*.—Strong.

*Stem aspect*.—An average angle of 60° to vertical.

*Internode length*.—An average of 4.7 cm.

*Branching*.—Well-branched, 1 main stem and 5 secondary branches per main branch.

Foliage description:

*Leaf shape*.—Palmately lobed, reniform to orbicular in outline.

*Leaf division*.—Simple.

*Leaf base*.—Hastate.

*Leaf apex*.—Narrow acute.

*Leaf fragrance*.—None.

*Leaf venation*.—Palmate, young upper surface 179A, young lower surface 180A, mature upper and lower surface 146D in color.

*Leaf quantity*.—An average of 12 (6 pairs) per lateral branch.

*Leaf margins*.—Biserrate, 5 lobes, occasionally 7, sinus depth deep, sinus orientation is convergent.

*Leaf arrangement*.—Opposite.

*Leaf aspect*.—Flat, leaves in an average angle of 70° to lateral branch.

*Leaf attachment*.—Petiolate.

*Leaf surface*.—Texture of both surfaces glabrous and smooth, upper surface very slightly glossy, lower surface slightly glossy, main veins of young leaves sparsely covered with a thin pubescence on both surfaces; an average of 0.4 mm in length, too small to measure.

*Leaf size*.—Average of 7.8 cm in length and 8.5 cm width.

*Leaf color*.—Young leaves upper surface; 179A, young leaves lower surface; 180A, mature upper surface; 137A to 137B, mature lower surface; 138A, fall color; upper surface a blend of 178A and 181A, lower surface 180A.

*Petioles*.—Average of 4.2 cm in length and 0.9 mm in diameter, both surfaces moderately glossy, strong, upper surface color; 180B, changing to 181A at the proximal end, fading to 179C at the distal end, lower surface color; 180B, fading to 152D at the distal end, base 151A.

*Stipules*.—None.

Inflorescence description: None produced to date.

Fruit and seed: None produced.

It is claimed:

1. A new and distinct cultivar of *Acer palmatum* tree named 'SONKOOT6' as herein illustrated and described.

* * * * *